(12) United States Patent
Pinneo et al.

(10) Patent No.: US 9,883,946 B2
(45) Date of Patent: Feb. 6, 2018

(54) COMPOSITE PROSTHETIC SURFACES

(71) Applicant: SPARKLE MEDICAL LLC, Portola Valley, CA (US)

(72) Inventors: John Michael Pinneo, Portola Valley, CA (US); Roy McDonald, San Mateo, CA (US); Charles K. Lim, Menlo Park, CA (US)

(73) Assignee: Sparkle Medical LLC, Portola Valley, CA (US)

( * ) Notice: Subject to any disclaimer, the term of this patent is extended or adjusted under 35 U.S.C. 154(b) by 34 days.

(21) Appl. No.: 14/823,776

(22) Filed: Aug. 11, 2015

(65) Prior Publication Data

US 2016/0045318 A1 Feb. 18, 2016

Related U.S. Application Data

(60) Provisional application No. 62/036,683, filed on Aug. 13, 2014.

(51) Int. Cl.
*A61F 2/30* (2006.01)
*A61F 2/32* (2006.01)
(Continued)

(52) U.S. Cl.
CPC ...... *A61F 2/30965* (2013.01); *A61F 2/30767* (2013.01); *A61F 2/32* (2013.01); *A61L 27/34* (2013.01); *A61L 27/446* (2013.01); *A61F 2002/30001* (2013.01); *A61F 2002/30016* (2013.01); *A61F 2002/30026* (2013.01); *A61F 2002/30682* (2013.01);
(Continued)

(58) Field of Classification Search
CPC ...... A61F 2/30; A61F 2/32; A61F 2/38; A61F 2/40; A61F 2002/30016; A61F 2002/30026; A61F 2002/30685; A61F 2002/30934; A61F 2310/00167
See application file for complete search history.

(56) References Cited

U.S. PATENT DOCUMENTS 5,571,202 A 11/1996 Mathys et al.
5,645,601 A * 7/1997 Pope ................... A61F 2/30767
623/23.39
(Continued)

FOREIGN PATENT DOCUMENTS

CN 103 007 356 A 4/2013
WO WO 9814140 A1 4/1998

OTHER PUBLICATIONS

TW Office Action dated Apr. 27, 2016 as received in Application No. 104126295 (English Translation), 11 pgs.
(Continued)

*Primary Examiner* — Brian Dukert
(74) *Attorney, Agent, or Firm* — Maschoff Brennan

(57) ABSTRACT

A composite article (e.g., prosthesis) and method of preparing the article is provided. An article may include a body having a matrix of a first hardness having a plurality of particles of a second hardness embedded in the matrix in fixed locations, the second hardness being harder than the first hardness, and the matrix having an external wear surface with a portion of the particles being proximal to or exposed at the external wear surface. The matrix with the particles may improve the life and durability of the article.

24 Claims, 10 Drawing Sheets

(51) Int. Cl.
        A61L 27/34          (2006.01)
        A61L 27/44          (2006.01)
(52) U.S. Cl.
        CPC .............. A61F 2002/30934 (2013.01); A61F
                    2310/00167 (2013.01); A61L 2420/04
                    (2013.01); A61L 2430/02 (2013.01); A61L
                                            2430/24 (2013.01)

(56)                    References Cited

U.S. PATENT DOCUMENTS 6,793,681  B1       9/2004   Pope et al.
    2003/0129257  A1*       7/2003   Nies .................... C08K 3/36
                                                                424/724
    2007/0202351  A1        8/2007   Justin et al.
    2007/0208427  A1*       9/2007   Davidson ............ A61F 2/30767
                                                                623/22.15
    2008/0255674  A1       10/2008   Rahaman et al.

OTHER PUBLICATIONS

TW Office Action dated Oct. 12, 2016 as received in Application No. 104126295 (English Translation), 15 pgs.
Anon, Health at a Glance 2011: OECD Indicators 2011.
Bowers, A. (2006). Orthopedics Data Compendium: Use, Cost, and Market Structure for Total Joint Replacement, 1-92.
Finneran, S., Hudon, R., Quintal, R., & Torok, M. (2011). Demand for Total Knee Replacements in the United States: A Preliminary Investigation.
Kubo, K., Clarke, I. C., Sorimachi, T., Williams, P. A., Donaldson, T. K., & Yamamoto, K. (2009). Aggressive 3rd-body wear challenge to highly crosslinked polyethylene: A hip simulator model. Wear, 267(5-8), 734-742. doi:10.1016/j.wear.2009.01.029.
Lavernia, C.J., Hernandez, V.H., Rossi, M. D. (2007). Payment analysis of total hip replacement. Current Opinion in Orthopaedics, 18(1) pp. 23-27.

McGloughlin, T. M., & Kavanagh, A. G. (2000). Wear of ultra-high molecular weight polyethylene (UHMWPE) in total knee prostheses: a review of key influences. Proceedings of the Institution of Mechanical Engineers. Part H, Journal of Engineering in Medicine, 214(4), 349-359. http://www.ncbi.nlm.nih.gov/pubmed/10997056.
Oral, E., & Muratoglu, O. K. (2007). Radiation cross-linking in ultra-high molecular weight polyethylene for orthopaedic applications. Nuclear Instruments and Methods in Physics, 265(1), 18-22. doi:10.1016/j.nimb.2007.08.022.
Puertolas, J. A., Martinez-Nogues, V., Martinez-Morlanes, M. J., Mariscal, M. D., Medl, Lopez-Santos, C., & Yubero, F. (2010). Improved wear performance of ultra high molecular weight polyethylene coated with hydrogenated diamond like carbon. Wear, 269(5-6), 458-465. doi:10.1016/j.wear.2010.04.033.
Wood, W., & Zhong, W. (2010). Mechanical and Wear Properties of UHMWPE Nanocomposites Filled With Carbon Nanofillers, 1-2. retrieved from http://wjoe.hebeu.edu.cn/ICCE-17%20proceedings%20Hawaii%20USA/Wood,%20W.%20(Washington%20St.U.,%20Pullman)%20%201131.pdf.
Buford, A., & Goswami, T. (2004). Overview of Metal-on-Polyethylene, Metal-on-Metal, and Ceramic Hip Wear Mechanisms. Journal of the Mechanical Behavior of Materials. doi:10.1515/JMBM.2004.15.1-2.73.
Fisher, J., Ingham, E., Jennings, L., Jin, Z., Tipper, J., & Williams, S. (2011). Tribological Aspects: To Wear or Not to Wear. In J. P. Vidalain, The CORAIL® Hip System (vol. 21, pp. 217-223). Springer Verlag. doi:10.1007/978-3-642-18396-6_7.
Huo, M. H. (2010). Disparity in revision total hip replacement: clinical outcome, cost, and surgeon work force. Current Orthopaedic Practice, 21(2), 149.
Pokorny, A., & Knahr, K. (2011). Tribology in Total Hip Arthroplasty. (K. Knahr) (pp. 99-109). Berlin, Heidelberg: Springer Berlin Heidelberg. doi:10.1007/978-3-642-19429-0_9.
International Search Report and Written Opinion, as issued in connection with International Patent Application No. PCT/US/2015/045081, dated Nov. 14, 2015, 11 pgs.

* cited by examiner

COMPOSITE PROSTHETIC SURFACES

CROSS-REFERENCE

This patent application claims priority to U.S. Provisional Application No. 62/036,683 filed Aug. 13, 2014, which provisional application is incorporated herein by specific reference in its entirety.

BACKGROUND

Prosthetic joints are biomedical devices that replace all or a portion of bone and cartilage in a joint, and thereby restore, improve, or prolong the useful function of that joint. Prosthetic joints are commonly implanted into human patients to mitigate degraded function of such major joints as hips, knees, shoulders, and the like. Like biological joints, prosthetic joints bear mechanical loads while facilitating relative movement of the opposed portions of the joint. This capability of a prosthetic joint enables critical locomotor activities, where for example a knee prosthetic joint can facilitate walking, bending the knees to stoop, and any other common function of the knee joint.

The use of prosthetic joints continues to grow, in part due to increasing numbers of elderly and in part because the benefits of joint prostheses are being extended to younger patients. Wear life of a prosthetic joint can be important in elderly patients, as revision procedures to replace worn joints become less-well tolerated with increasing age. Wear life is similarly important in younger prosthetic recipients, as the joints are exposed to greater mechanical stresses associated with more athletic lifestyles of the young and there may be a need for the prosthetic joint to last longer as the recipient ages.

Unlike biological joints, prosthetic joints do not have means of self-repair and are therefore subject to wear. Wear includes attrition of prosthetic joint materials due to mechanical and/or chemical effects on the joint surfaces that rub against each other. As wear proceeds, the function of a prosthetic joint may degrade to a significant degree and may require replacement in a revision operation. The worn prosthetic joint may also become more susceptible to catastrophic failure, and particulate materials worn from the prosthetic joint components may damage nearby tissues, potentially causing osteonecrosis and consequent joint failure.

Prosthetic joint wear is a complex process, and may be driven by mechanical stresses developed on the joint. These stresses include static stresses (e.g., such as would be developed by standing) and dynamic stresses (e.g., as would be caused by walking or running). These stresses wear prosthetic joint components and limit the joint's useful service life.

Therefore, it would be advantageous to have a prosthetic joint that has enhanced wear resistance for extended usefulness without needing a replacement.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1:
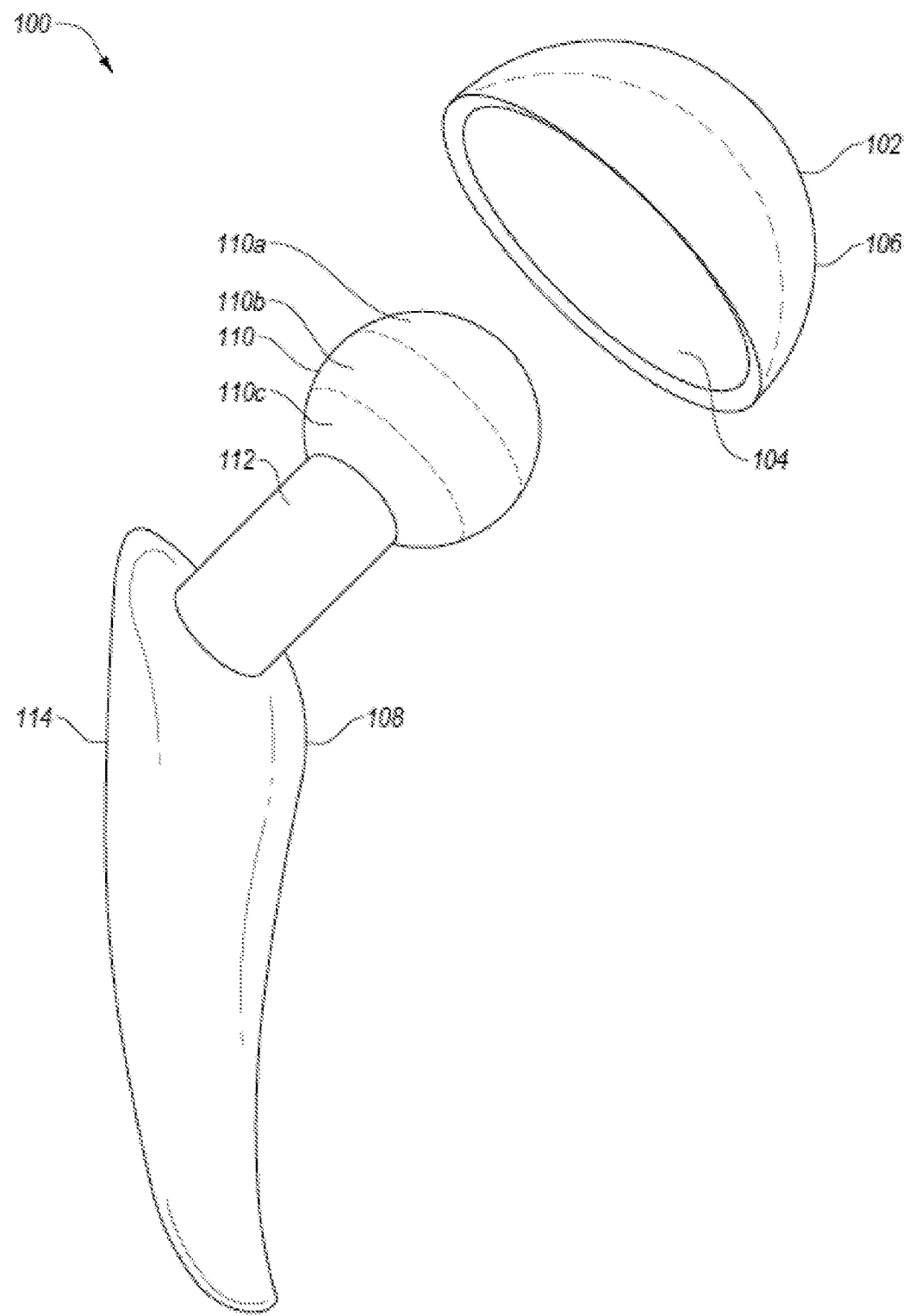
FIG. 1 is a diagram of an embodiment of a total hip prosthesis.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein and illustrated in the figures, can be arranged, substituted, combined, separated, and designed in a wide variety of different configurations, all of which are explicitly contemplated herein.

Generally, the present technology relates to compositional modifications of prosthetic implants that improve the life and durability of the prosthetic implant. In one aspect, the compositional modifications can be applied to any prosthetic implant that is implanted into a living organism. The prosthetic implants can be single implants that are implanted alone (e.g., intervertebral implant) or implant systems that are implanted and operate together (e.g., prosthetic joint). The compositional modifications can inhibit mechanical wear of the prosthetic implant, such as prosthetic joints, so that one or more surfaces of the prosthetic implant inhibit wear or degradation. The wear or degradation can be reduced by use of hard particles that are disposed in a matrix at various portions of prosthetic implant that are subject to wear. For example, for a single implant, the one or more surfaces that may contact bone may have the compositional modification. In another example, an implant system can include two or more implant components that slide or rub against each other, and the surfaces of one or a portion of or all of the implant components subject to such sliding or rubbing can include the compositional modification. The compositional modification can utilize a common prosthetic implant material and embed a harder material therein, where the harder material can be in the form of particles distributed throughout the matrix, such as at the surface of the matrix so as to be exposed.

Additionally, it has been found that the compositional modification can be applied to other articles of manufacture (e.g., conveyer belts, floor covering materials, plastic bearings, sanders, etc.) other than just prostheses. That is, the compositional modification can be applied to non-biological and/or non-medical articles of manufacture that include an exposed substrate or surface that can beneficial have the compositional modification. The compositional modification can increase the wear of surfaces that rub or slide against other surfaces. The compositional modification can beneficially be any matrix having particles that are harder than the matrix, such as the matrix being metal, ceramic, or plastic, and the particles being hard particles, such as diamond. The plastic matrix having the diamonds can be a useful example. As such, any surface that is part of a wear mechanism can include the compositional modification as described herein.

The compositional modification having the matrix with the harder particles can be used for a component that is used as a wear mechanism, such as any wear mechanism having a wear surface. Such a wear mechanism component can include hard abrasive particles that are dispersed throughout a softer matrix material, such as epoxy resins or rubber. For example, the matrix having the hard particles can be used to form grinding wheels or any other device having a wear surface. Initially, such grinding wheels against a work piece where excess matrix material is rapidly worn away to expose previously masked abrasive particles to the work piece. Following the removal of excess matrix material, regression of the abrasive-loaded matrix grinding wheel surface is governed by the interaction of exposed abrasive particles with the work piece material. So long as dispersed abrasive particles exhibit good interface adhesion to the surrounding matrix, the particles remain in place as they wear away. The wear rate of such grinding wheels is much slower than the wear rate of wheels made solely from the matrix material without dispersed hard abrasive particles. Additionally, the matrix having the hard particles can be applied to any component having a wear surface, such as a surface that slides against another surface. Accordingly, any substrate having a surface can have the matrix with the hard particles on the surface.

Previously, diamond has been utilized in prior attempts to improve prosthetic implants. For example, in U.S. Pat. No. 6,793,681, a mixture of metal and diamond particles is sintered under extreme heat and pressure. However, this technology is not sufficient for application to plastics or different particle concentration profile or gradients other than homogenous distribution. Also, the technology is not useful when chemically modifying the surface of the diamond, such as with biomolecule. As such, the present technology with the compositional modification is an improvement over the art as described herein.

The compositional modifications can be implemented on any surface on any type of prosthetic implant. However, the compositional modifications can be used on surfaces that slide or rub against bone or another implant. Some examples of prosthetic implants that can use the compositional modifications are prosthetic joints, where the compositional modification can be applied to all surfaces or a portion of a surface for a joint (e.g., joint surface) and thereby improve or prolong the useful function of the prosthetic joint. The prosthetic joints with the compositional modification can be implanted into human patients or animals to restore function of such major joints as hips, knees, shoulders, and the like. Like biological joints, the prosthetic joints bear mechanical loads while facilitating relative movement of the two opposed portions of the joint, where the surfaces that facilitate the relative movement can have the compositional modification. The compositional modification improves durability of these surfaces and facilitates locomotor activities, such as walking, bending the knees to stoop, and the like for a knee joint.

The prosthetic joints with the compositional modification can improve the longevity and usefulness over prior prosthetic joints. The prosthetic joints with the compositional modification can improve duration wear life, which can be important to elderly patients because revision procedures to replace worn prosthetic joints are not well tolerated with increasing age. The improved wear life can also be useful in younger prosthetic recipients, as the joints are exposed to greater mechanical stresses associated with more athletic lifestyles of the young, and the longer duration may allow younger recipients to have a prosthetic joint for the duration of their lives without needing a revision procedure.

In the prosthetic joints with the compositional modification, wear of the surfaces may be inhibited by inhibition of attrition of the material on the wear surface of the joint materials due to mechanical and/or chemical effects. That is, the compositional modification inhibits degradation of the prosthetic. The compositional modification can inhibit wear of the prosthetic surfaces and inhibit degradation thereof so as to avoid any need to replace the prosthetic in a revision operation. The compositional modification may be less susceptible to catastrophic failure so that the prosthetic joint can be capable of withstanding higher levels of mechanical stresses. Also, the compositional modification may result in less particulate materials being abraded from the surface so that there are less particles that are released from the prosthetic joint, where less particles can reduce damage to nearby tissues, and thereby inhibit osteonecrosis and consequent joint failure.

The compositional modification can inhibit the impact of mechanical stresses developed on the joint and improve the prosthetic joint's useful service life. While only certain examples of prosthetic joints are described herein, such as the prosthetic hip joints, the compositional modification can be applied to any prosthetic implant or prosthetic joints. As such, the compositional modification can be applied to other types of prosthetic implants or prosthetic joints that are subject to wear.

In one embodiment, the compositional modification can be applied to the components of a complete hip prosthesis, which generally includes two major components: one component being a partial sphere mounted on a stub that replaces the patient's femoral head; and one component being a cup-shaped component, such as the acetabular cup, which replaces the patient's acetabulum. The compositional modification can be applied to any portion of the components that form a ball-and-socket system that emulates the function of the biological joint they replace. The compositional modification can be applied to the region between the prosthetic femoral head and the opposed prosthetic acetabular cup, and thereby both sides of the articular interface can include the compositional modification. This allows for the region over which sliding motion of the opposed surfaces occurs to have the compositional modification to improve slidability with reduced wear. In one example, a matrix made from ultrahigh molecular weight polyethylene (UHMWPE) can be impregnated with the hard particles and applied to the surfaces of the articular interface, which results in the two principal opposed moving surfaces on each side having the compositional modification. However, the particle impregnated matrix can be applied to all or a portion of the complete hip prosthesis.

In one embodiment, the compositional modification can be applied to the components of a partial hip prosthesis, which generally includes components having functions similar to those of total hip prostheses in that they replace damaged surfaces on the opposed acetabulum and femoral head. When partial hip prostheses having the compositional modification are employed, the compositional modification can provide hip resurfacing. The compositional modifications can inhibit prosthetic wear and improve the useful life of the hip resurfacing. Similar to the total hip replacement prostheses, the partial prostheses can include a component made from UHMWPE plastic impregnated with hard particles that is used as one or both of the two principal opposed moving surfaces.

The matrix material that results in the compositional modification can be prepared from a variety of materials that are commonly used to fabricate prosthetic joints or other implants, and are biocompatible. The matrix materials can include various metals (e.g., titanium or CoCr alloys), ceramics (e.g., alumina), and plastics such as ultrahigh molecular weight polyethylene (UHMWPE), or other materials known or developed. These matrix materials can be impregnated with the hard particles and used in various combinations, including metal-on-metal, ceramic-on-ceramic, and metal or ceramic on UHMWPE plastic. The hard particles can be of various types, and such hard particles are harder than the matrix material into which they are impregnated. This allows for different hard particles to be used in different matrix materials, so that different combinations can be prepared.

In one embodiment, a prosthetic joint can include a metal or ceramic matrix for a femoral head that engages a UHMWPE matrix of an acetabular cup. The matrix of the femoral head and/or matrix of the acetabular cup can include the hard particles, or only the matrix of the acetabular cup can include the hard particles. As such, the matrix of the acetabular cup can include the hard particles so that the plastic cup does not wear more rapidly than the harder and less chemically reactive femoral head material with or without the hard particles. This allows for only one component (e.g., acetabular cup component) or both components (e.g., femoral head component) to have the matrix with the hard particles.

In one embodiment, the UHMWPE having the hard particles can include the matrix having properties that are improved by exposure to radiation during its formulation. This may be coupled with thermal treatments that further improve surface wear rates of the matrix. The resulting UHMWPE materials with the hard particles can have improved wear rates.

The composite material having the matrix impregnated with hard particles can improve the wear life of components employed in prosthetic joints. The hard particles can be any biocompatible particles that are harder than the matrix material. That is, the additive particles are harder than the materials to which they are added and are strongly fixed in place within the material surrounding them. When used in joint prostheses, components incorporating such hard particle additives in a matrix are worn away at rates that are determined primarily by the wear rate of the hard particulate additives rather than by the wear rate of the softer materials in which they are embedded.

Various types of hard particles can be used, which can be determined based on the matrix into which they are embedded. Diamond particles are one material in the class of biocompatible particulate materials that may be employed in any matrix. Silicon carbide is another material that can be employed in most matrix materials. Other hard materials in the form of particles exhibiting biocompatibility may be used. Additionally, stainless steel, titanium, titanium alloys (e.g., titanium-aluminum-niobium), or other metals may be used as the particles when included in a hard plastic like UHMWPE. Ceramic particles may also be included in plastic matrix materials.

In one aspect, the hard matrix material of one component (e.g., femoral head prosthesis) may be the particle of the other component (e.g., acetabular cup).

The beneficial utilities of prosthetic joints employing the compositional modification can include, but are not limited to: reduced mechanical wear on some or all prosthetic components and surfaces thereof; extended duration of prosthetic clinical lifetime; reduction and/or elimination of the need for revision procedures; reduction of costs associated with use of prosthetic joints; reduced dependence on exceptional surgical skill to achieve excellent clinical results; enhanced utility of prostheses for athletic or physically active patients; and expanded design alternatives for more advanced joint prostheses.

The surface of the prosthetic having the compositional modification can be configured similar to a grinder. Accordingly the compositional modification can include abrasive particles (e.g., hard particles) that are dispersed throughout much softer matrix material similarly to grinding wheels. At the first use of such a prosthetic with the grinder-like surface, excess matrix material is rapidly worn away, exposing previously masked abrasive particles to bone or another prosthetic component. Following the removal of excess matrix material, regression of the abrasive-loaded matrix surface is governed by the interaction of exposed abrasive particles with bone or another prosthetic component. So long as dispersed abrasive particles exhibit good interface adhesion to the surrounding matrix, said abrasive particles remain in place as they wear away. The wear rate of such a compositionally modified surface is much slower than the wear rate of surfaces made solely from the matrix material without dispersed hard abrasive particles.

Further, because exposed hard particles (e.g., diamond particles) are small and either exhibit smooth surfaces initially or become smooth after a brief 'run-in' or 'wear-in' period, they act to polish the opposing bone or prosthetic (e.g., prosthetic femoral head surface), maintaining a smooth surface known to be advantageous in extending wear life of prosthetic joint implants. It will be appreciated by those skilled in the art that the particle loading volume percent or exposed surface area percent, mean particle diameter, particle aspect ratio, and maximum particle diameter may be varied to meet the requirements of a particular application without departing from the limits of this disclosure.

The prosthetic implant can be any implant that is implanted into a subject. However, the implant may especially be suited when designed and used to be in contact with bone or another implant. While the prosthetic implant can be of any kind, the descriptions herein for a prosthetic hip joint are exemplary for the functionality that can be broadly applied to the prosthetic arts.

FIG. 1 illustrates selected features of an embodiment of a total hip prosthesis 100 that can include the compositional modification. The prosthesis 100 is shown to have an acetabular prosthesis 102 and a femoral prosthesis 108.

While the entirety of one or both of the acetabular prosthesis 102 and femoral prosthesis 108 can include the compositional modification on external regions thereof, only select portions or multiple portions may include the compositional modification. The acetabular prosthesis 102 can include the acetabular cup 104 having the compositional modification and/or the femoral prosthesis 108 can include the femoral ball 110 having the compositional modification. That is, one or both of the contacting surfaces of the total hip prosthesis 100 that contact and slide with respect to each other include the compositional modification. The acetabular prosthesis 102 may also include the acetabular shell 106 having all or a portion thereof with the compositional modification. The femoral ball 110 may include only the contacting and sliding hemisphere 110a marked by the dashed line with the compositional modification, or the compositional modification may extend over the curvature region 110b marked by the second dashed line, or over the entire waning region 110c so that the entirety of the exposed surface of the femoral ball 110 is covered. In one option, the femoral neck 112 may also include the compositional modification. In another option, the femoral stem 114 may also include the composition modification. Accordingly, the surfaces of the prosthesis 100 that contact and slide may be covered with the compositional modification, the portions of the prosthesis 100 that contact bone (e.g., acetabular shell 106 and/or femoral stem 114) may also include the compositional modification to improve retention into the bone, or the portions therebetween (e.g., femoral neck 112 may include the compositional modification.

In some instances it may be economically advantageous to only have one or more smaller regions having the compositional modification and in other instances it may be worthwhile to cover all exposed surfaces with the compositional modification, such as when the compositional modification improves structural integrity of the prosthesis. In any embodiment, any wear element of the prosthesis can include the compositional modification so that the compositional modification protects the femoral ball 110 and/or the acetabular cup 104 as they rotate or slide with respect to each other.

Figure 2:
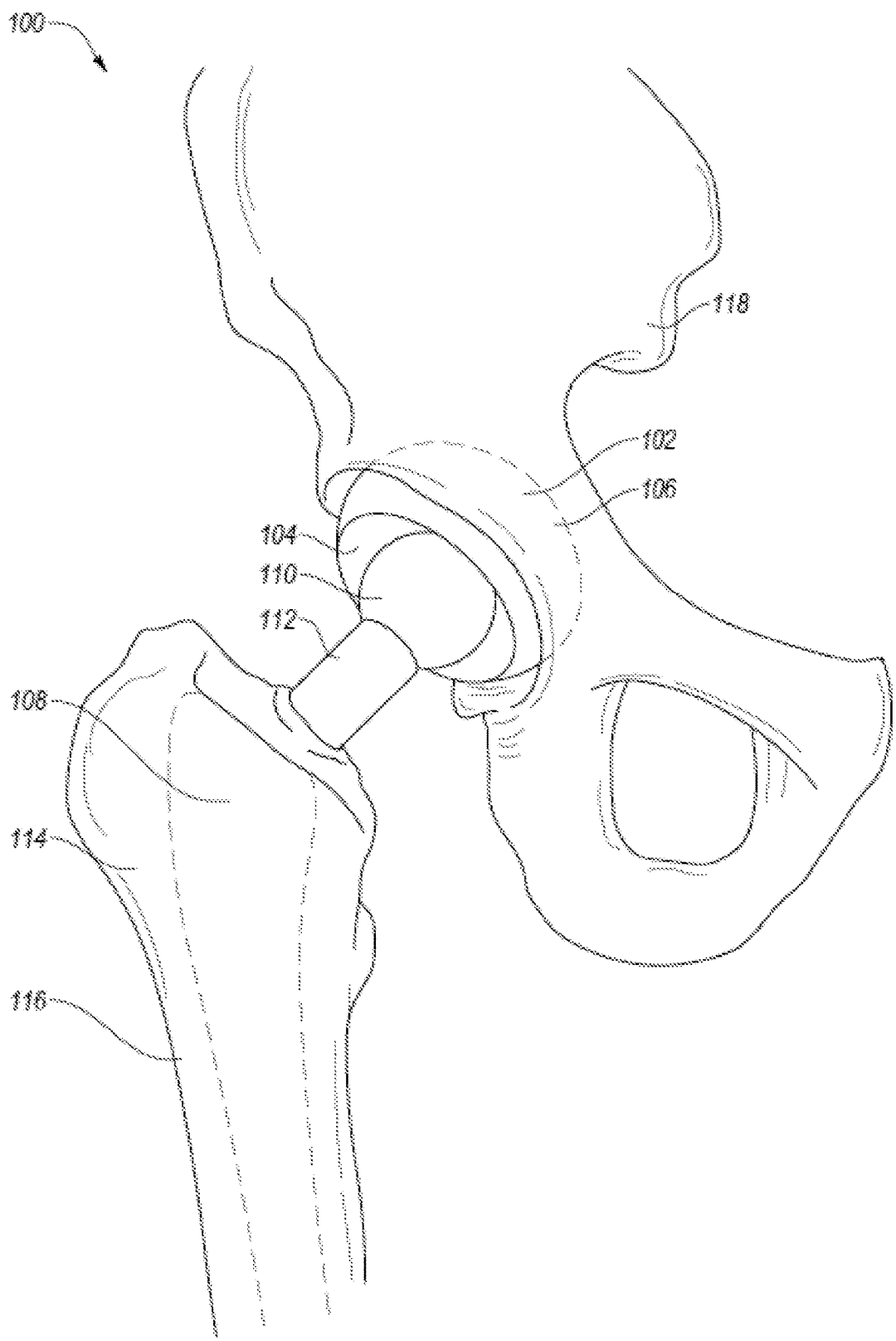
FIG. 2 is a diagram of an embodiment of a total hip prosthesis implanted into a body.

FIG. 2 illustrates an embodiment of the total hip prostheses 100 implanted into the femur 116 and hip 118 bones.

Figure 3:
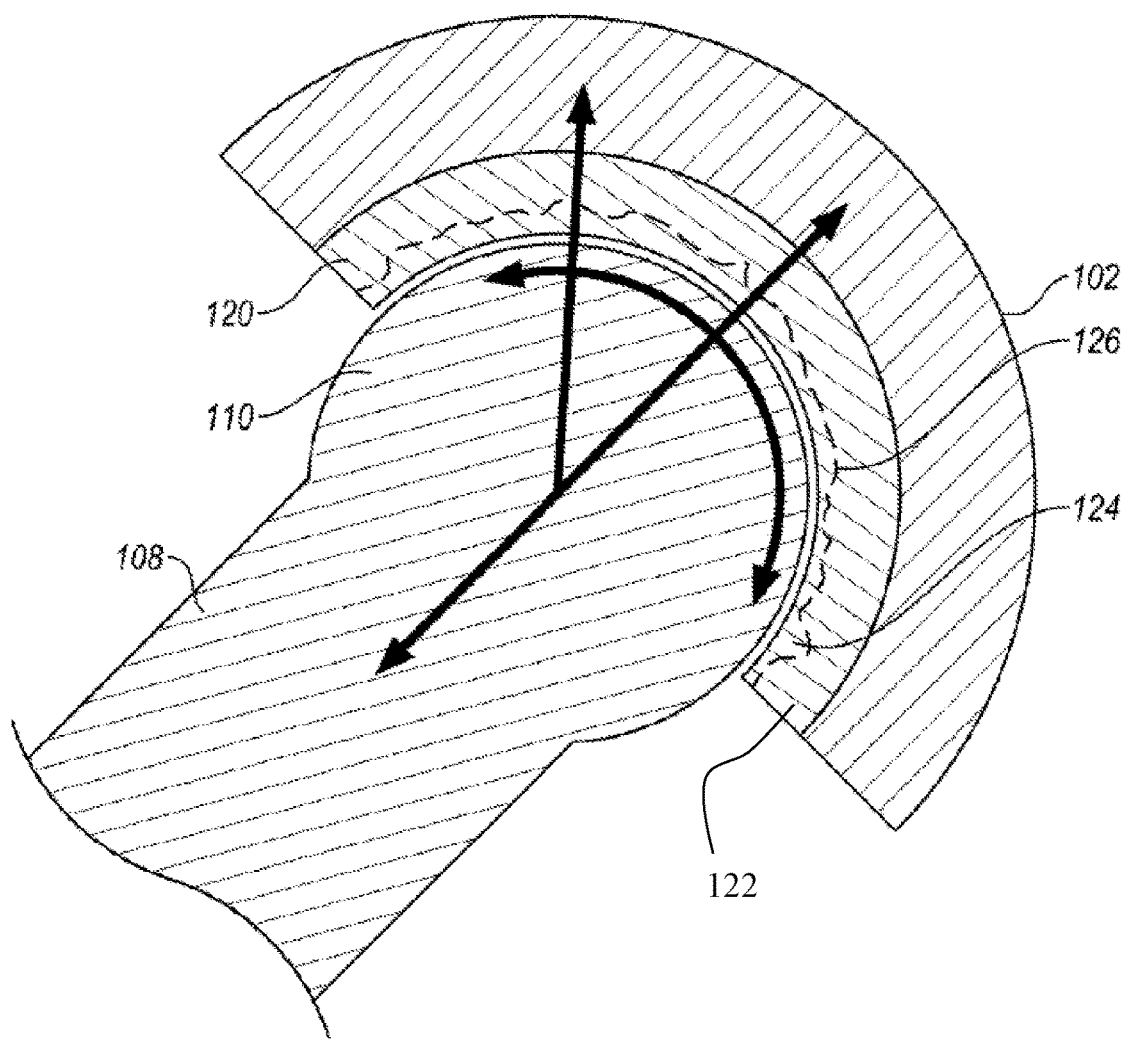
FIG. 3 is a diagram of an embodiment of rotatable and slidable coupling of an acetabular prosthesis and femoral prosthesis of a total hip prosthesis.

FIG. 3 illustrates an embodiment of a hip prosthesis 300 that has the acetabular prosthesis 102 functionally coupled with the femoral prosthesis 108. As such, the acetabular prosthesis 102 includes an acetabular cup 120 that is formed of a first region 122 closer to the acetabular shell 106 and a second region 124 between the first region 122 and femoral ball 110. The arrows show general movement motions of the femoral ball 110 relative to the acetabular cup 120. The acetabular shell 106 may be made of a material, such as polymer, composite, or metal, which can be coupled with another material of the first region 122, such as polymer (e.g., UHMWPE). However, the acetabular shell 106 and first region 122 may be the same material or other different materials or material combinations. The first region 122 may also have the compositional modification described herein; however, often the first region 122 is a solid material without particles embedded therein. The second region 124 includes a matrix material impregnated with hard particles so that the second region provides the compositional modification. The femoral ball 110 is shown without the compositional modification. The matrix material of the second region 124 can be any matrix material and the particles embedded therein may be any particle that is harder than the matrix material. The particles may be of the same material as the femoral ball 110 or other material that is harder than the matrix, which may also be harder than the femoral ball 110. While the interface 126 (e.g., shown by the dashed line) between the first region 122 and second region 124 may be smooth, the interface 126 is shown to be jagged with recesses and protrusions, optionally with overhangs or undercuts, to facilitate mechanical bonding or attachment of the first region 122 to the second region 124.

Figure 4:
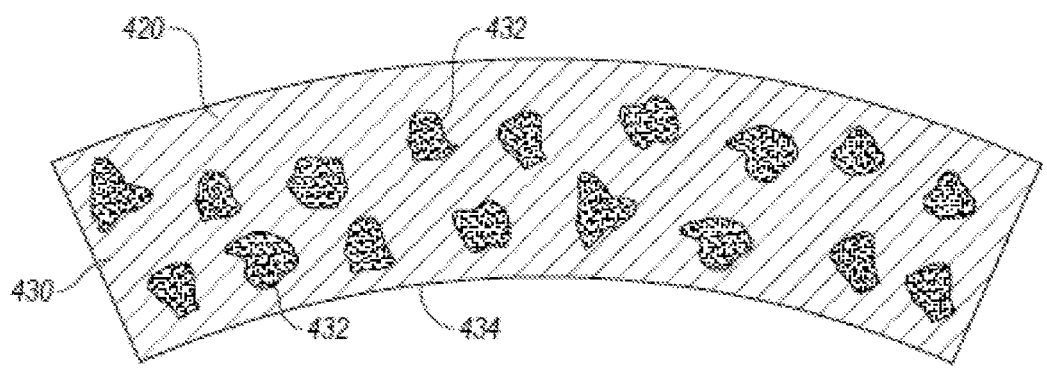
FIGS. 4-4B are diagrams of embodiments of implants that have compositional modifications with different wearing surfaces.

FIG. 4 illustrates a portion of an implant that has the compositional modification. Here, the illustration is of an embodiment of an acetabular cup 420 that is similar to the second region 124 of FIG. 3 for the acetabular cup 120. As shown, the acetabular cup 420 includes the matrix 430 having the particles 432 embedded therein. This results in the matrix 430 being impregnated with a distribution of particles 432. As shown herein, the cup surface 434 (e.g., that is associated with the femoral ball) is not shown with any particles 432 forming a part of the cup surface 434 or extending therethrough. This may show a manufacture state before the prosthesis is used or early stages of use. Some wear is acceptable to wear the matrix 430 down to the particles 432, and then the particles control the wear rate. Any prosthetic surface can be configured as shown in FIG. 4, whether flat, concave or convex, or even complicated shapes.

Figure 4A:
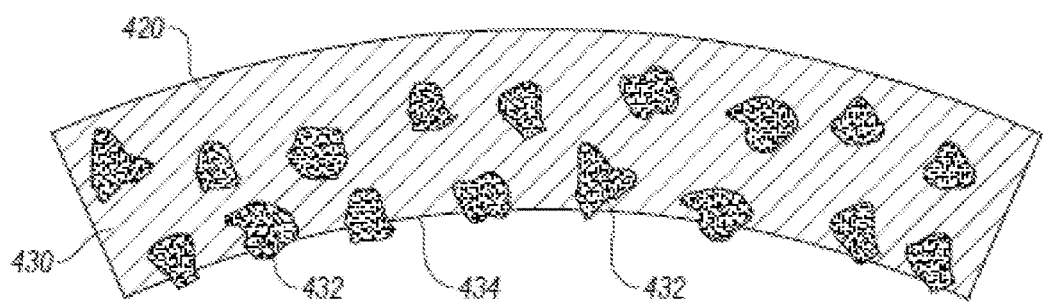

FIG. 4A illustrates a portion of an implant that has the compositional modification. Here, the illustration is of an embodiment of an acetabular cup 420 that is similar to the acetabular cup 420 of FIG. 4, except that the particles 432 protrude from the cup surface 434. As shown, the acetabular cup 420 includes the matrix 430 having the particles 432 embedded therein. This results in the matrix 430 being impregnated with a distribution of particles 432. As shown herein, the cup surface 434 (e.g., that is associated with the femoral ball) is shown with particles 432 protruding from the cup surface 434 or extending therethrough. This may show a either a manufacture state before the prosthesis is used and/or a use state. For example, the matrix 430 may be prepared with some of the particles 432 protruding therefrom, and the particles 432 control the wear rate. If or when the particles 432 are worn down or are abraded away from the matrix 430, the matrix 430 can abrade until new particles 432 are exposed. Any prosthetic surface can be configured as shown in FIG. 4A, whether flat, concave or convex, or even complicated shapes.

Figure 4B:
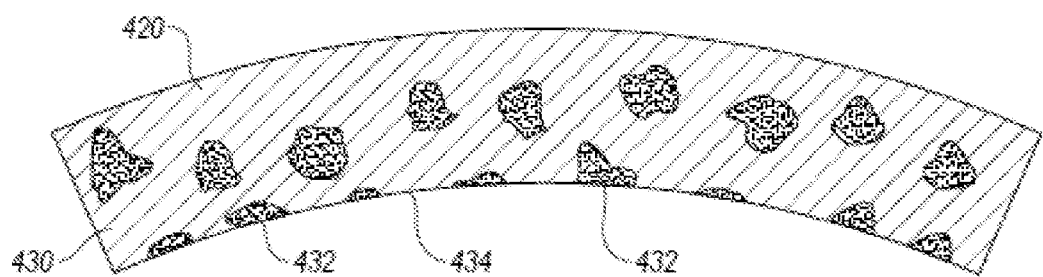

FIG. 4B illustrates a portion of an implant that has the compositional modification. Here, the illustration is of an embodiment of an acetabular cup 420 that is similar to the acetabular cup 420 of FIGS. 4 and 4A, except that the particles 432 are continuous with the cup surface 434. That is, the particles 432 have exposed surfaces 432a that are smooth and continuous with cup surface 434 of the matrix 430 material. As shown, the acetabular cup 420 includes the matrix 430 having the particles 432 embedded therein with some particles 432 being worn down so that the exposed surfaces are continuous with the matrix 430. This results in the matrix 430 being impregnated with a distribution of particles 432 with some of the particles 432 being exposed. As shown herein, the cup surface 434 (e.g., that is associated with the femoral ball) is shown with particles 432 smoothly continuous with the cup surface 434. This may show either a manufacture state before the prosthesis is used and/or a use state. For example, the matrix 430 may be prepared with some of the particles 432 protruding therefrom and then ground down to make the smooth cup surface 434. If or when the particles 432 are worn down or are abraded away from the matrix 430, the matrix 430 can abrade until new particles 432 are exposed, which can then be ground down by wear to again appear as shown in FIG. 4B. Any prosthetic surface can be configured as shown in FIG. 4B, whether flat, concave or convex, or even complicated shapes.

In one aspect, the particles can have any shape. This can include the particles being diamond and having common diamond shapes, or silicon carbide with common shapes thereof, as well as any other particles with their respective shapes. Examples of the particle shapes can be round, oblong, regular, acicular, tabular, irregular, or another shape. In some instances tabular shapes can be helpful for manufacturing smooth exposed surfaces.

In one embodiment, the particles can be homogenously distributed in the matrix, which is substantially shown in FIGS. 4-4B. However, the particles can be in a random or inhomogeneous distribution. The particles may also be in a gradient distribution, where the gradient can be a continuous or step gradient that is linear or non-linear, sinusoidal, or any other gradient configuration. In some instances, it may be beneficial to have a lower concentration near the exposed surface so that the surface becomes more abrasive and more particles are exposed as the prosthesis wears down so that the wear rate decreases as more is worn away. In another instance, it may be beneficial to have a higher concentration near the exposed surface so that the new surface is more abrasive with a lower wear rate, and then over time the wear rate may increase as the concentration of particles decreases.

Figure 5:
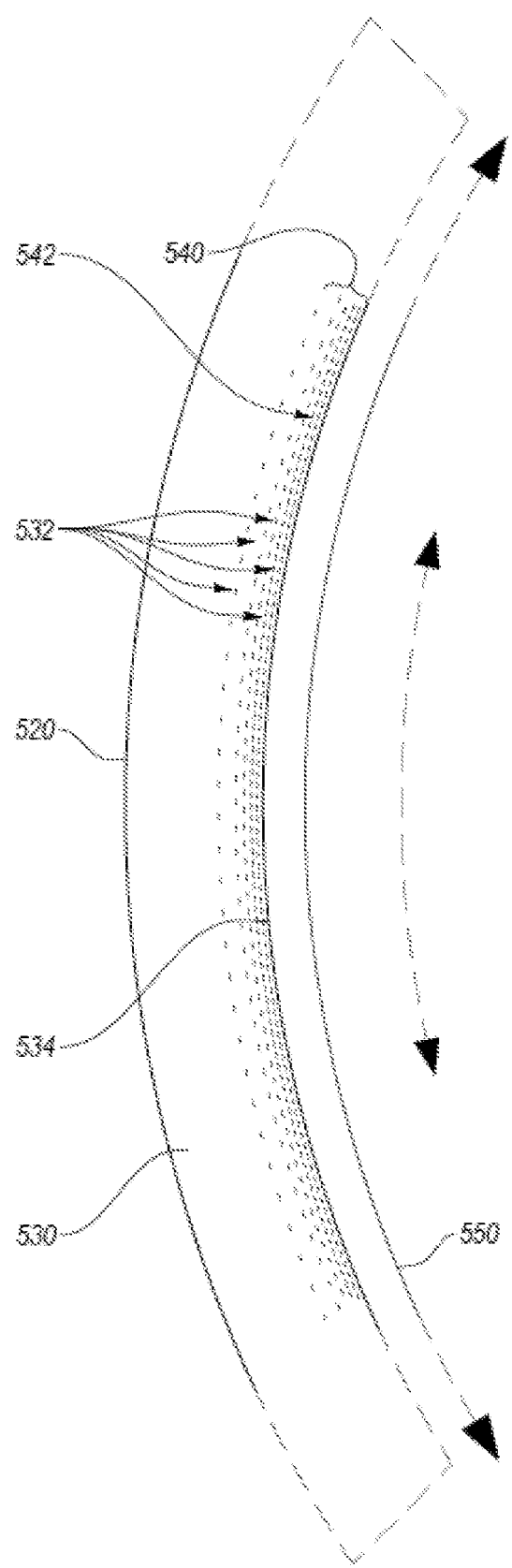
FIG. 5 is a diagram of an embodiment of an implant with a matrix with a gradient of the embedded particles.

As shown in FIG. 5, an embodiment includes the particles having a higher concentration near the exposed surface and where there is a particle gradient that decreases in concentration moving inward from the exposed surface. Here, the illustration is of an embodiment of an acetabular cup 520 that is similar to the acetabular cup 420 of FIGS. 4-4B, except that the particles 532 are in a gradient distribution 540 relative to the cup surface 534. That is, the particles 532 have a higher concentration 542 near the cup surface 534 and then a decreasing concentration away from the cup surface 534. This results in the matrix 530 being impregnated with a gradient distribution 540 of particles 532 with some of the particles 532 being exposed. As shown herein, the cup surface 534 (e.g., that is associated with the femoral ball) is shown with particles 532 smoothly continuous with the cup surface 534. This may show either a manufacture state before the prosthesis is used and/or a use state. The femoral head wear surface 550 is also shown with the dashed arrow showing a representative direction of rotation relative to the cup surface 534. While the gradient distribution 540 is shown to only expend partially through the matrix 530, the gradient may extend all the way through the matrix 530. Any prosthetic surface can be configured as shown in FIG. 5, whether flat, concave or convex, or even complicated shapes.

Figure 6:
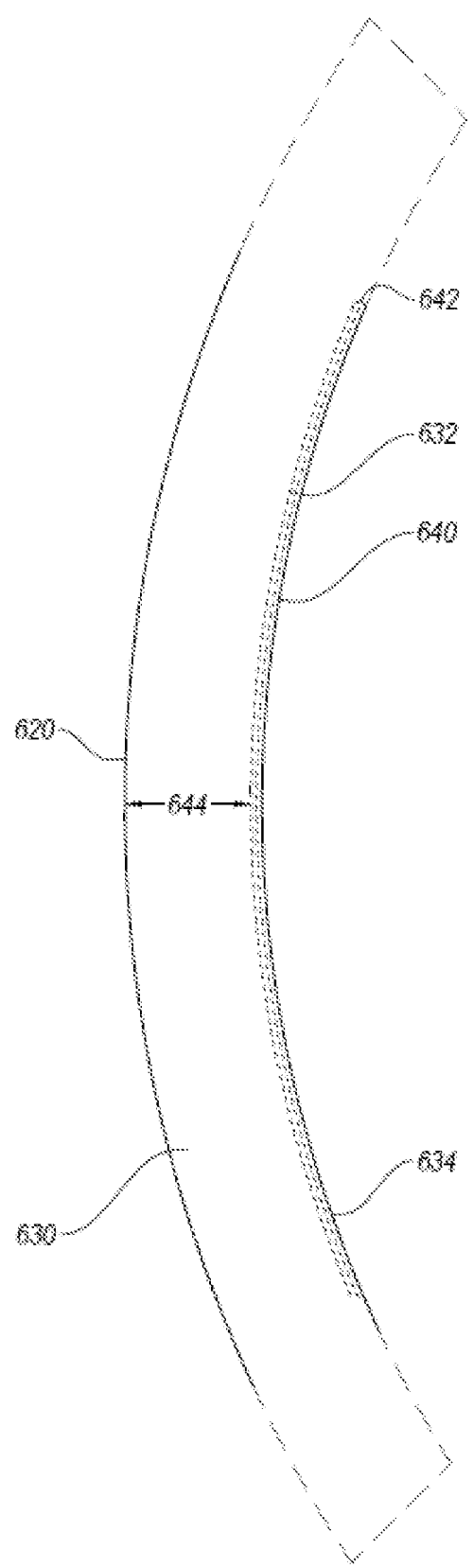
FIG. 6 is a diagram of an embodiment of an implant with a matrix a band of particles at a wear surface.

As shown in FIG. 6, an embodiment includes the particles 632 in a band 640 near the exposed surface and the band 640 can be homogenous, inhomogeneous, or in a gradient distribution. Here, the illustration is of an embodiment of an acetabular cup 620 that is similar to the acetabular cup 420 of FIGS. 4-4B, except that the particles 632 are in a band 640 relative to the cup surface 634. That is, the particles 632 are in a defined region near the cup surface 634 with a defined dimension 642 and are not outside of the band 640, which can be a region devoid of particle 632, said region having a dimension 644. This results in the matrix 630 being impregnated with a band 640 of particles 632 with some of the particles 632 being exposed. As shown herein, the cup surface 634 (e.g., that is associated with the femoral ball) is shown with particles 632 smoothly continuous with the cup surface 634. This may show either a manufacture state before the prosthesis is used and/or a use state. Any prosthetic surface can be configured as shown in FIG. 6, whether flat, concave or convex, or even complicated shapes.

Figure 7:
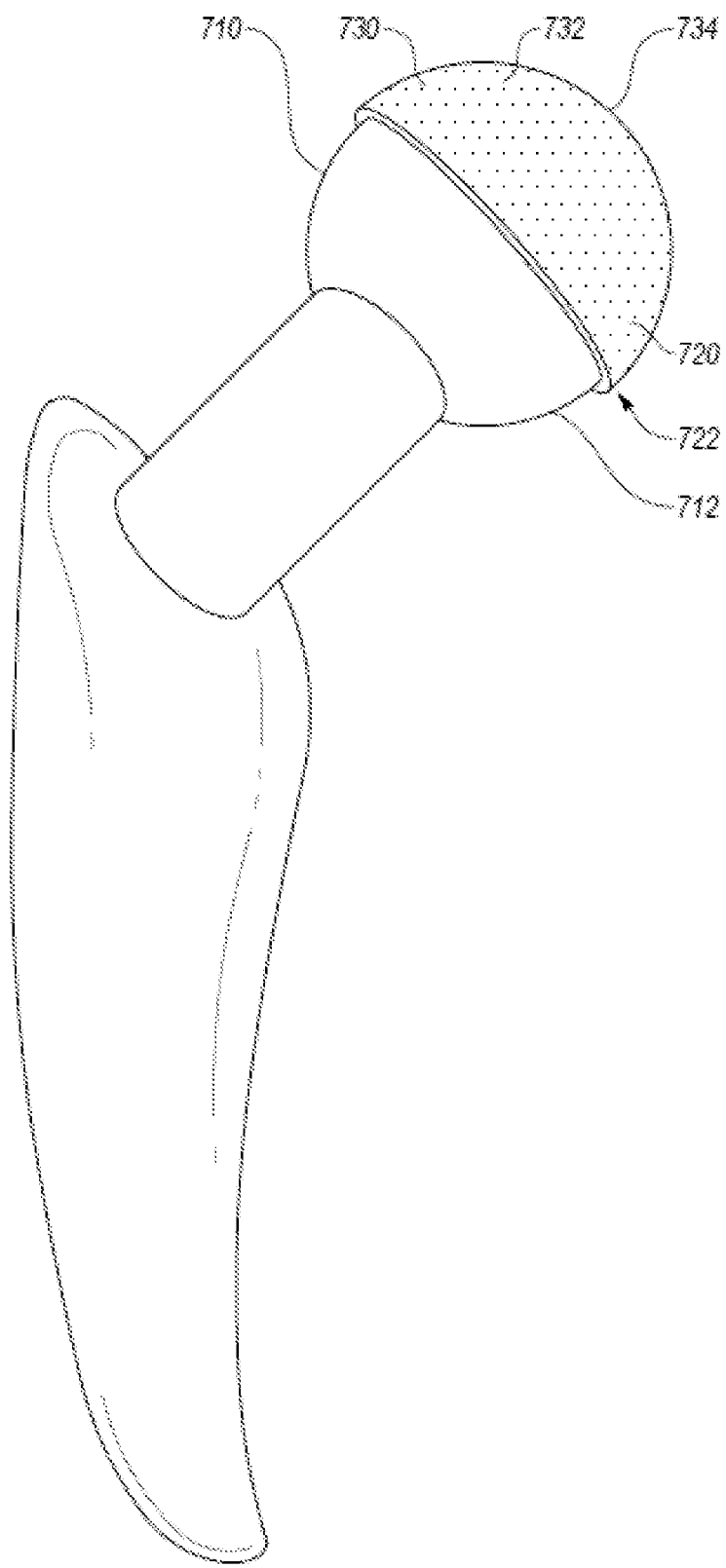
FIG. 7 is a diagram of an embodiment of femoral implant with a coating of a matrix with embedded particle.

FIG. 7 shows an embodiment of a femoral ball 710 having a coating 720 of the composition having the matrix 730 and the particles 732 distributed therein. Here, the coating 720 is applied to the femoral ball substrate 712. The coating is applied in a manner to cover the first region 722 of the femoral ball, consistent with FIG. 1. The coating provides a femoral surface 734 that can mate with and rotate with respect to an acetabular cup, such as any of the embodiments described herein. Also, any prosthetic can be coated as shown or described in connection with FIG. 7. The coating 720 can be configured as any of the compositional modifications described herein, such as having a homogeneous distribution, inhomogeneous distribution, gradient distribution, or the like, with the particles 732 being completely embedded in the matrix 730 (e.g., FIG. 4), particles 732 protruding from the matrix 730 (e.g., FIG. 4A), or the particles 732 having smooth surfaces that are smooth and continuous with the external surface of the matrix 730 (e.g., FIG. 4B). Any prosthetic surface can be configured as shown in FIG. 7, whether flat, concave or convex, or even complicated shapes.

Figure 8:
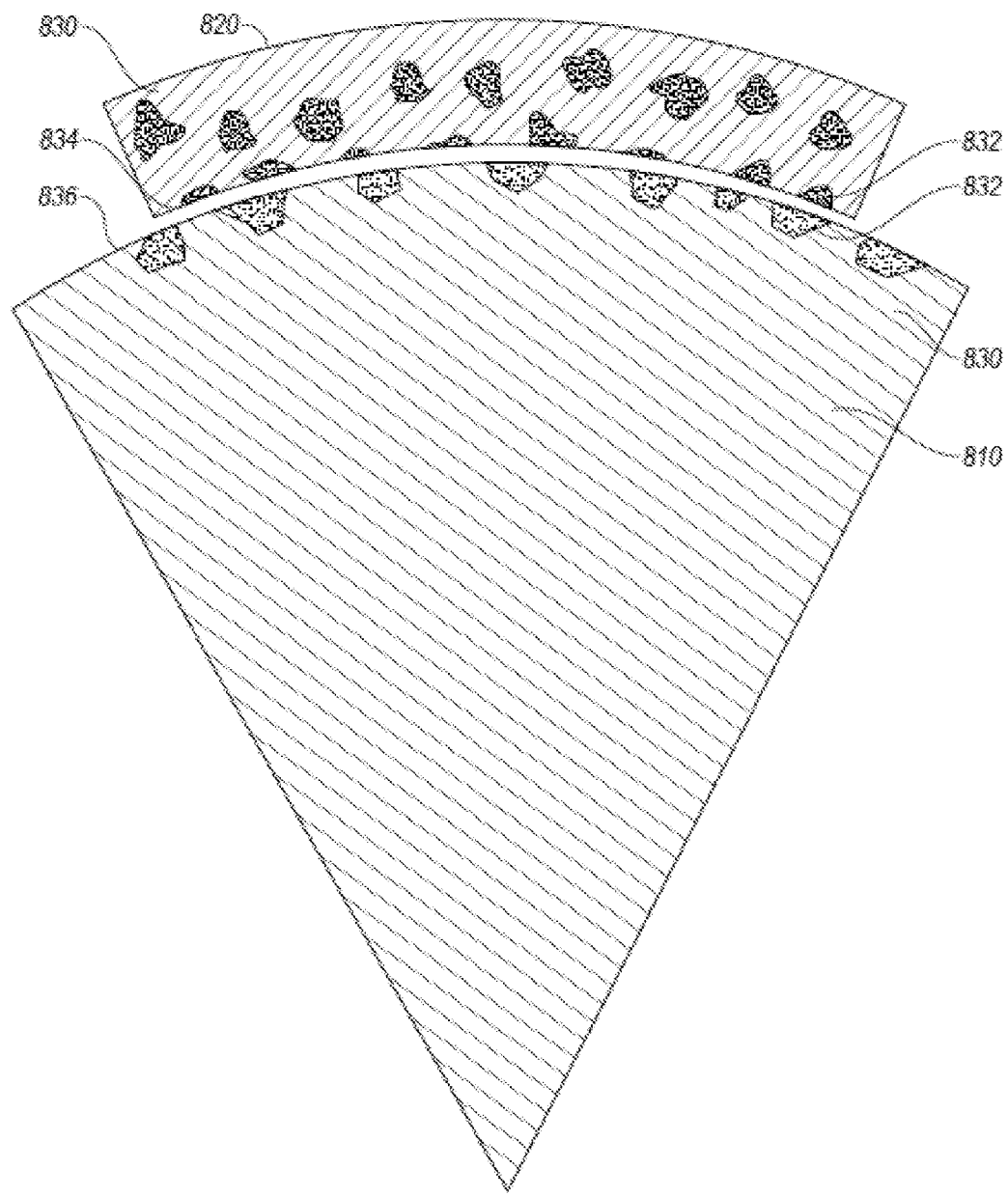
FIG. 8 is a diagram of an interface of an embodiment of an acetabular implant with a matrix having embedded particles and an embodiment of a femoral implant with a matrix having embedded particles.

FIG. 8 illustrates portions of the prosthetic acetabular cup 802 and the prosthetic femoral ball 810. As shown, each has a matrix 830 having the particles 832 located therein. The acetabular cup 802 includes the particles 832 smooth and continuous with the matrix 830 at the cup surface 834, and the femoral ball 810 includes the particles 832 smooth and continuous with the matrix 830 of the ball surface 836. This configuration allows the cup surface 834 to slide smoothly relative to the ball surface 836 without significant wear or damage to the prosthesis. The cup surface 834 and ball surface 836 can be configured consistent with any embodiment of a prosthesis having the compositional modification of the matrix having the particles distributed therein. Also, the opposing surfaces can be applied to any type of prosthetic system for any joint.

In one embodiment, the particles are diamond particles that are embedded in a UHMWPE matrix material. The matrix having the particles can be located at an acetabular cup wear region of a prosthesis, and include the diamond particles distributed in the UHMWPE material. The matrix can be prepared so that the wear surface is unexposed to wear processes and the wear surface thereof exhibiting unexposed diamond particles underlying UHMWPE surface material. Also, the wear region can include the diamond particles distributed in the UHMWPE matrix material with exposed diamond particles protruding from the matrix, which can be obtained following removal of overlying UHMWPE by manufacturing or initial wear processes. The wear region can include the diamond particles distributed in the UHMWPE matrix material that has planarization or smoothing of exposed diamond particles to a run-in or wear-in process. There are many types of particle morphologies that are operative in the current invention as wear reduction additives to UHMWPE material. The discussion of diamond particles can apply to any particle that is harder than the matrix and the UHMWPE can be replaced by any other suitable matrix.

In one embodiment, the diamond particles can be included in a UHMWPE matrix within a limited region that includes the wear surface, but excludes a portion of the remainder of the UHMWPE matrix. As such, the particles can be in a band of the matrix. This configuration allows for improvement of local wear properties at the wear surface without changing properties of the UHMWPE or the entire matrix or prosthesis.

In one embodiment, the diamond particles can be included in step gradients so that there are a plurality of bands from the wear surface that have different concentrations of particles in each band.

A joint prosthesis can include a wear surface interface that has a diamond-on-diamond sliding particle interface, such as for example between a diamond-enhanced acetabular cup and a diamond-enhanced femoral head, the sliding and loads being mainly carried by opposed planarized regions (e.g., smooth continuous surface) of the diamond particles in the matrix.

In one embodiment, a portion of a prosthesis that is mounted into or onto bone or cartilage can be devoid of the particle-containing matrix. For example, the region of the femoral prosthesis (e.g., femoral stem) that is inserted into the femur can be devoid of the particle-containing matrix, and the acetabular shell can be devoid of the particle-containing matrix. This may include the prosthesis having the wear surfaces that wear or rub or slide or otherwise contact another prosthetic component to have the particle-containing matrix promote improvement in wear rates. The portion of a prosthesis that is mounted into or onto bone or cartilage may be configured to promote cellular ingrowth and may include growth factors, such as bone or cartilage growth factors.

In one embodiment, a matrix material can include a defined volume percent or area percent on a wear surface of the hard particles. The volume percent can be defined as the volumetric amount of the particle compared the volumetric amount of the matrix. The area percent can be defined as the area amount of the particles compared to the area amount of the matrix on a wear surface or any external surface of the prosthesis. The volume percent or area percent can range from 0.1 to 60 percent, or greater than 0.5 percent, or greater than 1 percent, or greater than 2 percent, or greater than 5 percent, or greater than 10 percent, or greater than 20 percent, and/or less than 60 percent or less than 50 percent or less than 40 percent or less than 30 percent, or any combination thereof. In one example, the particles can be diamond at 2 percent by volume or by area.

In one embodiment, the ranges and upper/lower concentration limits of the particles in the matrix can vary for different uses and various concentrations may be suitable for different uses. The concentration of particle should be less than an upper limit beyond which basic mechanical integrity will be degraded. This upper limit is below the concentration in which the matrix has a concentration of particles that causes the matrix to breaks easily. On the lower concentration limit, there will be some particle loading fraction below which no useful increase in wear resistance occurs. Accordingly, the ranges and upper/lower limits are given as examples without limitation. The concentration of particles being 10%-20% by volume has shown to be suitable; however, there are uses where less than 10% or more than 20% by volume may be suitable or desirable.

In one embodiment, the particles can have a diameter of at least 0.1 nanometer to less than 500 nm, or greater than 1 nm, or greater than 10 nm, or greater than 20 nm, or greater than 30 nm, or greater than 40 nm, or greater than 50 nm, and/or less than 400 nm, or less than 300 nm, or less than 200 nm, or less than 100 nm, or less than 75 nm, or less than 60 nm, or any combination thereof. Examples can include from 40-50 nm. Also, the size of the particles in a matrix can vary significantly over a range of tens of nanometers. In one aspect, the size distribution of particles in a matrix can be limited to about 10 nm difference. The values recited herein may be ranges of diameters or the mean diameters of the particles in the matrix.

In one embodiment, the aspect ratio of the particle can range as needed. An example can include an aspect ratio of 1; however, the aspect ratio can range up to 10. For example, acicular particles can be used, as can fibrous particulates formed by deposition of diamond over non-diamond fibrous substrates, including silicon carbide, silicon nitride, and other materials known to be compatible with diamond deposition.

In one embodiment, the wear life of plastic prosthetic components can be improved when made to include the matrix and harder particles as described herein. While metal and ceramic composite materials may also have improvements with the hard particles, the plastic components can be improved by being capable of being thinner. Metal and ceramic materials may also be thinner when including the hard particles; however, plastic components may beneficially be significantly thinner. For example, a method of designing a component can include obtaining a thickness of a prosthetic component, selecting a material having a matrix with hard particles for the component, determining one or more thinner thicknesses for the component, and testing to determine the minimum thickness of the component when the matrix having the hard particles. Such a method can be performed for metal, ceramic, or plastic components. The thickness when using the matrix with hard particles can be 95%, 90%, 80%, 75%, 50%, 40%, 30%, or 25% of the normal or original thickness, such as when compared to the matrix material without the particles. This allows for thinner components (e.g., plastic) to be employed, enabling broader ranges of prosthetic joint design and mechanical configuration.

The resulting mixed material of the matrix having the particle is formed into any prosthesis component, such as the acetabular cup component of a hip joint prosthesis. At least the surface of said component that opposes a bone or other prosthetic component (e.g., the prosthetic femoral head) can be processed (e.g., by polishing) to smooth protruding particles (e.g., diamond particles) so as to cause their exposed surfaces to be substantially parallel or smooth or continuous with the matrix of the component.

In one example, because diamond has a hardness far exceeding UHMWPE, after a short 'run-in' period during which any UHMWPE material overlying intermixed diamond particles is worn away, long-term regression of the wear surface is governed by wear of the diamond particles rather than by wear of the much softer UHMWPE, with the result that cup surface regression is decreased compared to UHMWPE not incorporating diamond dust. This applies to any type of particles in any type of matrix so long as the particles are harder than the matrix.

In embodiment, when the particles that have an aspect ratio greater than 1 are added to a matrix, the particles can be aligned in a preferential orientation by means known to the art, said means including orientation by electrostatic or magnetic means, or by mechanical deformation processes such as extrusion, in which velocity shear of the extruded medium tends to orient particles having greater than unity aspect ratios parallel to lines of isovelocity shear during extrusion.

In one embodiment, the particles can be synthetic diamond particles. The diamond particles can be prepared using means known in the art of diamond particle growth to provide substantial surface roughness, thereby enhancing the degree to which said diamond particles are retained or captured in the surrounding matrix material.

In one embodiment, the particles (e.g., diamond particles) can be subjected to chemical modification to modify the properties thereof. For the diamond particle example, the normally hydrogen-terminated surface can be chemically modified by any possible chemical means. The chemical modification can include attaching various chemical moieties such as polymers (e.g., polyethylene, polyethylene glycols, or other biocompatible polymers), biomolecules (e.g., drugs or markers or antibodies or growth factors), optical markers (e.g., radiopaque or colorimetric particles), or any other chemical modification. The chemical modification can be to enhance the degree to which the particles are retained or captured in the surrounding matrix material. It is contemplated that additional utility may be provided through alteration of the surface chemistry of diamond particles employed in our invention. This can include the addition of chemical moieties to the diamond surface, with one exemplary chemical moiety being fluorine, which may be added to diamond surfaces by exposure to fluorine plasmas generated, for example, by the action of microwave or radio frequency energy after methods known in the art of semiconductor manufacturing processes [Saito, et al, Antithrombogenicity of fluorinated diamond-like carbon films, *Diamond and Related Materials*, v. 14, pp. 1116-1119, 2005]. This can also include addition of biologically active materials such as pharmaceuticals, antibodies, antigens, bone growth stimulation factors and the like to the diamond surface, with one non limiting example being the addition of paclitaxel to diamond surfaces by, for example, covalent bonding methods [Liu, et. al, Covalent linkage of nanodiamond-paclitaxel for drug delivery and cancer therapy, *Nanotechnology*, v. 21, 2010].

In one aspect, the chemical modification can be useful for diamond particles. The diamond particles may be diamond dust. Such diamond particles can have their surfaces modified to facilitate stronger bonding with the matrix and/or retention in the matrix. For example, in order to facilitate bonding with a surrounding UHMWPE matrix material, some or all of the hydrogen atoms that normally terminate carbon bonds at diamond surfaces may be removed (by processes known in the art of surface modification of diamond, for example, heating the diamond to temperatures above about 800° Centigrade or exposing the diamond surface to atomic hydrogen as may be generated by tungsten filaments heated to over about 2,200° C. or by plasma dissociation of hydrogen or hydrogen-containing species (such as methane or ammonia), thereby leaving unterminated, chemically reactive carbon bonds on the diamond surface, said reactive carbon bonds being available for, and tending to form, bonds with hydrogen atoms that, with carbon, comprise the major portion of UHMWPE. The attachment can be covalent by replacement of the normal-hydrogen-terminated surface of the diamond with a substance (e.g., polymer or active group or linking group) that facilitates interactions, such as covalent or non-covalent bonding) between the matrix and the diamond particles.

In one aspect, the chemical modification can include a beneficial biomolecule (e.g., drug, antibody or growth factor) attached to the diamond particles. The attachment can be covalent by replacement of the normal-hydrogen-terminated surface of the diamond with a biomolecule with or without a linker to the diamond particles.

In one embodiment, the matrix may also include non-particulate additives. Such additives can be any time that can improve the composition and component made therefrom. The additives may include bioactive agents or any beneficial agent. Drugs, nutraceuticals, vitamins, or other agents can be included in the matrix. One example can include Vitamin E in a plastic (e.g., UHMWPE) matrix.

In one aspect, the chemical modifications can include an optically active tag or an optically visible tag attached to the diamond particles. The attachment can be covalent by replacement of the normal-hydrogen-terminated surface of the diamond with a substance that can be viewed by the naked eye or with the use of visualization equipment (e.g., X-ray, fluoroscopy, spectroscopy, or the like).

In one embodiment, the particles are added to a matrix material used in prosthetic joints, and the distribution of the particles is adjusted to provide differing local volume densities, or loading fractions, such as gradients or step gradients. The particles can be present at higher concentrations at the wear surface to obtain maximum wear resistance at that surface while reducing or eliminating particles distant from that wear surface.

In one embodiment, the prosthesis can include multiple bands of a matrix with particles, where the different bands have different matrix materials and/or different particles such that the bands are distinguishable. The distinguishing can be viewed by machinery often used for imaging inside bodies. Also, radiographic materials can be placed in certain layers so that the wear rate can be monitored, such as with X-ray or the like.

In one embodiment, a component of a prosthesis can be coated with an adherent layer of plastic (e.g. UHMWPE) that includes the particles. The coating can be over metal, ceramic, or plastic (e.g., UHMWPE without particles).

In embodiment, up to all of the particles intermixed into the matrix may be selected from particles having varied shapes and/or sizes and/or surface topologies and/or surface chemical functionalities. Also, different types of particles can be used, such as diamond and silicon carbide.

In one embodiment, a biocompatible lubricious particulate material (e.g., graphite) can be dispersed throughout the matrix along with the hard biocompatible particulate materials.

In one embodiment, the particle-containing matrix on a prosthesis is subjected to a run-in or wear-in process in which the embedded hard particles are exposed from the matrix and are smoothed and/or planarized so as to be continuous with the matrix. This can occur prior to the implantation or this process can occur after implantation.

The manufacture of the particle-containing matrix can result in a variation of concentration of said particles. The variation in concentration can be achieved by controlled distribution of the particles to enhance the utility of the prosthesis, such as by concentrating the particles at or near the wear surface. The high concentration of particles at the wear surface can maximize resistance of that surface to mechanical wear, while maintaining desirable properties in other regions of the prosthesis.

In embodiment, manufacture of the of the particle-containing matrix can include processing of it to cause hard biocompatible particles to become adherent to the wear surface, thereby conferring enhanced resistance to wear without the need to disperse said hard particles throughout the matrix material prior to fabrication of the prosthesis or prosthetic component having the particle-containing matrix. One example of such a process is mechanical burnishing, in which particle dust is carried on a rapidly rotating compliant structure, such as a rotary brush, the rotating structure being brought into contact with a surface to be endowed with adherent particles. Mechanical interactions drive small particles into the surface exposed to this process where the particles are retained in the surface. It will be appreciated by those skilled in the art that this process may be applied to metals and ceramics as well as plastics, such as UHMWPE.

In one embodiment, at least one surface of a component of an implanted joint prosthesis is adherently coated with a particle-containing matrix. The coating can provide a wear-resistant surface without the need for incorporation of wear-resistant particulates in the materials from which the prosthetic component is made. That is, the core of the prosthetic component is a certain material, which is coated with the particle-containing matrix. Examples of applying such a coating can include dipping, spraying, spinning, or otherwise distributing over the surface to be coated a molten layer of particle-containing matrix so as to form the adherent coating upon cooling.

In one embodiment, the process of preparing the prosthesis with the compositional modification can include coating the surface of prosthesis with a thin adherent layer of matrix material that contains dispersed particles. However, other methods of manufacture may be employed. In one aspect, the matrix can be prepared to have the particles distributed therein and then applied to a prosthesis. In one aspect, the matrix having the particles can be cast into the prosthesis. In one aspect, the matrix can be prepared and the particles can be penetrated into the matrix. In one aspect, the matrix can be prepared and the particles can be pressed under pressure into the matrix. In one aspect, multiple matrices can be prepared and the particles contained therein, and the matrices can be stacked, such as in a step change gradient configuration.

In one embodiment, a joint implant device can include: a first rigid bone-shaped structure with a wearing surface, the wearing surface having a matrix of a first biocompatible material having an external surface; and a plurality of biocompatible particles embedded in the matrix with a portion of the particles being exposed at and continuous with the external surface of the matrix. The wearing surface can have a rounded concave cup shape of a socket of a ball and socket joint. Also, the wearing surface can have a rounded convex partial sphere shape of a ball of a ball and socket joint. Additionally, the wearing surface can have the shape of a hinge joint.

The joint implant device can also include a second rigid bone-shaped structure with a second wearing surface shaped to fit together with the first rigid bone shaped structure. The second wearing surface can include a matrix of a second biocompatible material having an external surface; and a plurality of biocompatible particles embedded in the matrix with a portion of the particles being exposed at and continuous with the external surface of the matrix.

In one embodiment, the plurality of biocompatible particles can be inhomogeneously distributed through the matrix, such as in a gradient from an external surface of the matrix. Optionally, the gradient can include a high distribution of the plurality of biocompatible particles at the external surface of the matrix and essentially none of the plurality of biocompatible particles at an end of the gradient. Also, the plurality of biocompatible particles is only distributed in a part of the matrix.

In one embodiment, the plurality of biocompatible particles is regular, acicular, tabular, or irregular in shape. In one aspect, the plurality of biocompatible particles is preferentially oriented in the first biocompatible material. In one aspect, the plurality of biocompatible particles has substantial surface roughness. In one aspect, the plurality of biocompatible particles has been chemically modified to increase the degree to which it is retained or captured in the matrix.

In one aspect, the matrix can include other particles or materials, such as a plurality of lubricious particulate materials (e.g., graphite).

In one embodiment, a joint implant device can include a first rigid bone-shaped structure having an implant composition having a matrix of a first biocompatible material having an external surface and a plurality of biocompatible particles embedded in the matrix with a portion of the particles being exposed at and continuous with the external surface of the matrix. Alternatively, the particles can be embedded in the matrix and not exposed at a surface of the matrix, which allows for a wear-in process to expose the particles.

A process of preparing a joint implant device can include smoothing at least one embedded biocompatible particle in the matrix with or without smoothing the matrix.

Another process of manufacturing a joint implant device can include: mechanical burnishing a plurality of biocompatible particles on a rotating brush; bringing the brush into contact with a wearing surface of a joint implant device; and driving the plurality of biocompatible particles into the wearing surface of the joint implant device.

Example

In one example, it was demonstrated that the compositional modification having the matrix with the hard particles provided enhanced resistance to mechanical wear. The example included a plastic having diamond particles. Diamond particles having a diameter distribution less than 1 μm were mixed into a common two-part epoxy formulation ("Superhard Epoxy" product available from Tap Plastics, Inc.) to prepare samples having 10 volume % and 20 volume % incorporated diamond particles. This plastic system was selected for its ready availability and ease of achieving a relatively uniform dispersion of diamond particles. The results demonstrated herein apply to other plastics, such as UHMWPE, as well as to metals and composites.

After mixing diamond particles separately into the epoxy product's resin and hardener components, those components were combined and mixed according to the manufacturer's directions to initiate hardening. The mixed materials were then immediately poured into fluorocarbon plastic molds, cured for 1.5 hours at 100° F., and then recovered from their molds. A quantity of epoxy material was prepared at the same time using no diamond particles, but which was otherwise subjected to the same mixing, molding, and curing protocol as the diamond-loaded materials. This unloaded material was used to prepare wear samples having no diamond particles.

Wear samples that were produced included cylinders being 0.25 inches in diameter and 1.0 inch in length. In a test protocol emulating wear of prosthetic plastics in their normal use environment, samples were pressed against a cylindrical steel wear tool rotating at 300 RPM. The steel wear tool was a polished, hardened precision cylindrical shaft of 0.3125 inches in diameter and 3.00 inches in length. The tool was lightly scratched along its lengthwise axis to impart a surface texture needed to achieve mechanical wear.

Figure 9:
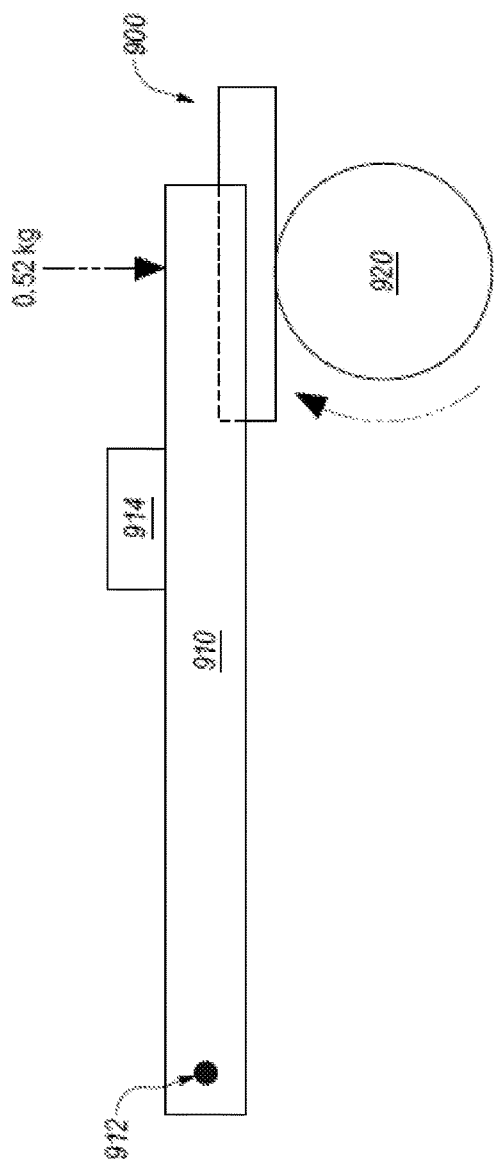
FIG. 9 is a diagram of an experimental system to study wear rates of wear samples by a wear tool.

Wear samples were fixed to an articulated holder that held each sample perpendicular to the wear tool and pressed each sample against the rotating wear tool with 0.52 kg of force as measured at the point of contact between the sample and the tool. A schematic depiction of the test arrangement may be seen in FIG. 9. FIG. 9 shows a wear sample 900 between the articulated holder 910 and wear tool 920 (e.g., steel wear tool). The articulated holder 910 has a pivot point 912 and a weight 914 that presses the wear sample 900 against the steel wear tool 920. An absorbent pad was saturated with an aqueous solution containing electrolytes and proteins to emulate a prosthetic joint use environment. This pad was placed in contact with the steel wear tool opposite the region of contact with the wear sample and supplied the wear interaction zone with a continuous fluid film.

Figure 10A:
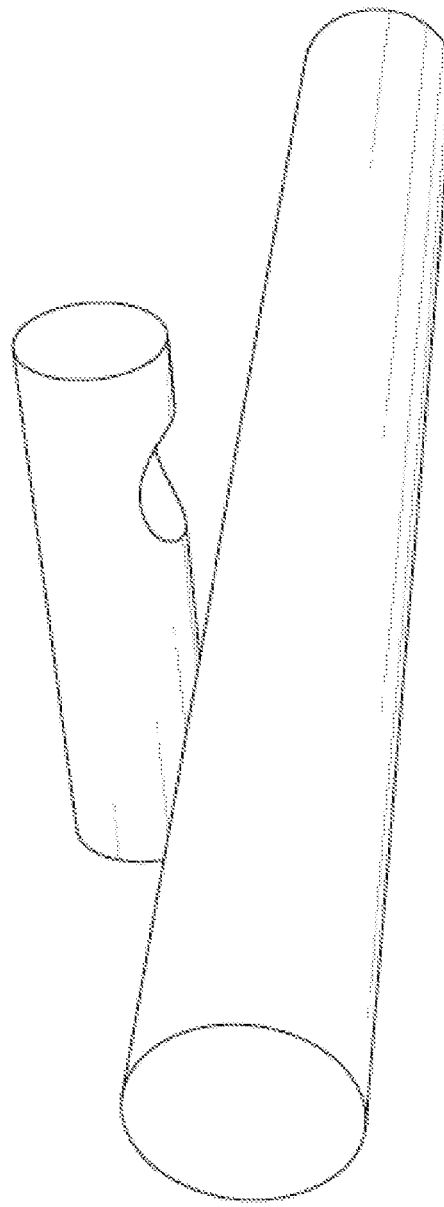
FIG. 10A shows a schematic representation of the wear tool forming a "U" shaped wear pattern on the wear sample.
Figure 10B:
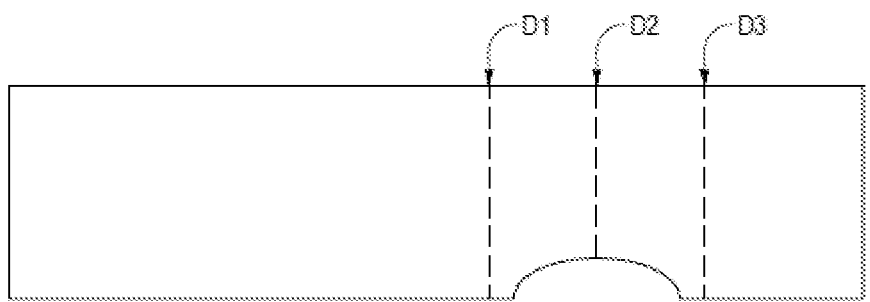
FIG. 10B shows a schematic diagram of the dimensions and shape of the wear pattern on the wear sample.

Each sample and the wear tool were cleaned with 99% isopropanol prior to testing. Test runs were timed and proceeded for approximately 40 minutes each. Following each test, wear patches were identified on the wear samples. These wear patches took the form of elliptical depressions in the wear samples. A schematic visualization of a worn sample having a "U" shaped wear pattern with the wear tool may be seen in FIG. 10A and in FIG. 10B. Wear patch depth was measured by measuring wear sample diameter at the center of the wear patch and compared to the unworn diameter at adjacent points to either side of the wear patch. A schematic depiction of this measurement protocol is shown in FIG. 10A where the dimension (e.g., depth) of the "U" shaped wear pattern is compared with the dimension (e.g., diameter) of the wear sample. No wear was noted on the steel wear tool. This can also include measuring the thickness of the wear sample at the "U" shape compared to the normal thickness (e.g., diameter) of the wear sample, such as shown in FIG. 10B to compare dimension D2 with dimension D1 and/or dimension D3.

Wear patch depth was used as an input parameter, along with the diameter of the steel wear tool, to calculate the volume of plastic sample material removed. This result, divided by the run duration, yielded the material removal rate in cubic inches/minute. Results are shown in Table 1. Wear removal rates in the two samples incorporating diamond particles were reduced by factors of approximately 100 and 1000 compared to the sample containing no diamond dust.

TABLE 1

| Sample Type | Wear rate, in$^3$/minute |
|---|---|
| No diamond particles | $2.13 \times 10^{-6}$ |
| 10 volume % diamond particles | $2.66 \times 10^{-9}$ |
| 20 volume % diamond particles | $1.66 \times 10^{-8}$ |

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions, or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A prosthesis comprising:
a prosthetic body having a biocompatible matrix of a first hardness having a plurality of biocompatible particles of a second hardness embedded in the biocompatible matrix in fixed locations, the second hardness being harder than the first hardness, and the biocompatible matrix having an external wear surface with a portion of the biocompatible particles being proximal to the external wear surface,
wherein the biocompatible particles have a diameter less than 500 nanometers,
wherein at least some of the biocompatible particles of the portion of particles are embedded in the biocompatible matrix with the external wear surface being devoid of the biocompatible particles.

2. The prosthesis of claim 1, wherein the prosthetic body is the biocompatible matrix with the plurality of biocompatible particles embedded therein.

3. The prosthesis of claim 1, wherein the prosthetic body includes a biocompatible material that is different from the biocompatible matrix, and the biocompatible matrix is coated on the prosthetic body.

4. The prosthesis of claim 1, wherein the biocompatible particles are homogenously distributed in a wear region of the matrix, the wear region including the external wear surface.

5. The prosthesis of claim 1, wherein the biocompatible particles are inhomogenously distributed in a wear region of the matrix, the wear region including the external wear surface.

6. The prosthesis of claim 1, wherein the biocompatible particles are distributed in a gradient distribution in a wear region of the matrix, the wear region including the external wear surface, and wherein the gradient distribution has a higher concentration nearer to the external wear surface and a lower concentration nearer to a center of the prosthetic body.

7. The prosthesis of claim 1, wherein the biocompatible matrix is ultrahigh molecular weight polyethylene (UHMWPE) and the particles are diamond biocompatible particles.

8. A method of preparing the prosthesis of claim 1, the method comprising:
preparing the prosthetic body to include the biocompatible matrix of the first hardness having the plurality of biocompatible particles of the second hardness embedded in the biocompatible matrix in fixed locations, the second hardness being harder than the first hardness, and the biocompatible matrix having an external wear surface with a portion of the biocompatible particles being proximal to or exposed at the external wear surface, wherein the biocompatible particles have a diameter less than 500 nanometer, wherein at least some of the biocompatible particles of the portion of particles are embedded in the biocompatible matrix with the external wear surface being devoid of the biocompatible particles.

9. The method of claim 8, further comprising:
preparing the prosthetic body to be the biocompatible matrix; and
embedding the biocompatible particles into the biocompatible matrix.

10. The method of claim 8, further comprising:
preparing the biocompatible matrix to include the biocompatible particles; and
coating the prosthetic body with the biocompatible matrix having the biocompatible particles.

11. A joint prosthesis system comprising:
a first prosthesis including a first prosthetic body having a first biocompatible matrix having a plurality of first biocompatible particles embedded in the first biocompatible matrix in fixed locations, the plurality of first biocompatible particles having a hardness that is harder than a hardness of the first biocompatible matrix, and the first biocompatible matrix having a first external wear surface with a first portion of the plurality of first biocompatible particles being proximal to or exposed at the first external wear surface; and
a second prosthesis including a second prosthetic body having a second biocompatible matrix having a plurality of second biocompatible particles embedded in the second biocompatible matrix in fixed locations, the plurality of second biocompatible particles having a hardness that is harder than a hardness of the second biocompatible matrix, and the second biocompatible matrix having a second external wear surface with a second portion of the plurality of second biocompatible particles being proximal to or exposed at the second external wear surface,
wherein the first external wear surface is configured to slidably and/or rotatably couple with the second external wear surface,
wherein the plurality of first biocompatible particles and plurality of second biocompatible particles have a diameter less than 500 nanometers,
wherein:
at least some of the biocompatible particles of the first portion of the plurality of first biocompatible particles are embedded in the first biocompatible matrix with the first external wear surface being devoid of the first biocompatible particles; and/or
at least some of the biocompatible particles of the second portion of the plurality of second biocompatible particles are embedded in the second biocompatible matrix with the second external wear surface being devoid of the second biocompatible particles.

12. The prosthesis system of claim 11, wherein;
the first prosthetic body is the first biocompatible matrix with the plurality of first biocompatible particles embedded therein; and/or
the second prosthetic body is the second biocompatible matrix with the plurality of second biocompatible particles embedded therein.

13. The prosthesis system of claim 11, wherein:
the first prosthetic body includes a first biocompatible material that is different from the first biocompatible matrix, and the first biocompatible matrix is coated on the first prosthetic body; and/or
the second prosthetic body includes a second biocompatible material that is different from the second biocompatible matrix, and the second biocompatible matrix is coated on the second prosthetic body.

14. The prosthesis system of claim 11, wherein:
the first biocompatible particles are homogenously distributed in a first wear region of the first biocompatible matrix, the first wear region including the first external wear surface; and/or
the second biocompatible particles are homogenously distributed in a second wear region of the second biocompatible matrix, the second wear region including the second external wear surface.

15. The prosthesis system of claim 11, wherein:
the first biocompatible particles are inhomogenously distributed in a first wear region of the first biocompatible matrix, the first wear region including the first external wear surface; and/or
the second biocompatible particles are inhomogenously distributed in a second wear region of the second biocompatible matrix, the second wear region including the second external wear surface.

16. The prosthesis system of claim 11, wherein:
the first biocompatible particles are distributed in a first gradient distribution in a first wear region of the first biocompatible matrix, the first wear region including the first external wear surface, and wherein the first gradient distribution has a higher concentration nearer to the first external wear surface and a lower concentration nearer to a center of the first prosthetic body; and/or
the second biocompatible particles are distributed in a second gradient distribution in a second wear region of the second biocompatible matrix, the second wear region including the second external wear surface, and wherein the second gradient distribution has a higher concentration nearer to the second external wear surface and a lower concentration nearer to a center of the second prosthetic body.

17. The prosthesis system of claim 11, wherein:
at least some of the biocompatible particles of the first portion of the plurality of first biocompatible particles are exposed at the first external wear surface with the first biocompatible matrix and the first portion of the plurality of first biocompatible particles forming a smooth and continuous first external wear surface; or
at least some of the biocompatible particles of the second portion of the plurality of second biocompatible particles are exposed at the second external wear surface with the second biocompatible matrix and the second portion of the plurality of second biocompatible particles forming a smooth and continuous second external wear surface.

18. The prosthesis system of claim 11, wherein:
at least some of the biocompatible particles of the first portion of the plurality of first biocompatible particles are exposed and protruding from the first external wear surface; or
at least some of the biocompatible particles of the second portion of the plurality of second biocompatible particles are exposed and protruding from the second external wear surface.

19. The method of claim 8, further comprising:
introducing the biocompatible particles to one or more compositions prior to the one or more compositions being:
polymerized into the biocompatible matrix having the plurality of biocompatible particles;
further polymerized into the biocompatible matrix having the plurality of biocompatible particles; or
processed into the biocompatible matrix having the plurality of biocompatible particles.

20. The prosthesis of claim 1, wherein the biocompatible particles have a diameter less than 100 nanometers.

21. The prosthesis of claim 1, wherein the biocompatible matrix includes a loading of biocompatible particles of less than 10% by volume.

22. The prosthesis of claim 1, wherein the biocompatible matrix includes a loading of biocompatible particles of between 10% to 20% by volume.

23. The prosthesis of claim 1, wherein the biocompatible particles have a size distribution that is within a difference of 10 nanometers.

24. The prosthesis of claim 1, wherein the biocompatible particles are non-covalently embedded within the biocompatible matrix.

* * * * *